United States Patent [19]

White

[11] Patent Number: 4,751,307

[45] Date of Patent: Jun. 14, 1988

[54] WITTIG-REACTION PROCESSES

[75] Inventor: Carl R. White, St. Louis, Mo.

[73] Assignee: Mallinckrodt, Inc., St. Louis, Mo.

[21] Appl. No.: 20,064

[22] Filed: Feb. 27, 1987

Related U.S. Application Data

[63] Continuation of Ser. No. 692,154, Jan. 17, 1985, abandoned.

[51] Int. Cl.$^4$ .................. C07D 489/100; C07C 37/02
[52] U.S. Cl. ........................................ 546/44; 546/46; 560/121; 560/210; 560/238; 560/260; 570/142; 585/357; 585/437; 585/469; 585/640
[58] Field of Search .............. 546/44, 46; 560/238, 560/260, 210, 121; 570/142; 585/357, 437, 469, 640

[56] References Cited

U.S. PATENT DOCUMENTS

| | | | |
|---|---|---|---|
| 3,162,639 | 12/1964 | Fishman | 546/44 |
| 3,814,768 | 6/1974 | Fishman | 546/44 |
| 3,883,488 | 5/1975 | Pearson et al. | 526/75 |
| 3,896,226 | 7/1975 | Fishman | 514/282 |
| 3,929,919 | 12/1975 | Evers et al. | 570/219 |
| 3,932,485 | 1/1976 | Surmatis | 560/238 X |
| 4,322,426 | 3/1982 | Hermann et al. | 514/282 |

FOREIGN PATENT DOCUMENTS

0631865  11/1961  Canada ........................... 585/469

OTHER PUBLICATIONS

Fieser, et al., Reagents for Organic Synthesis, John Wiley & Sons, Inc., New York, p. 41 (1967).
Kujita, et al., Chem. Pharm. Bull., vol. 12(10), pp. 1166–1171 (1964).
Pommer, The Wittig Reaction in Industrial Practice, Angewandte Chemie, International Edition in English, vol. 16, (1977), pp. 423–429.
The Merck Index of Chemicals and Drugs, Seventh Edition (1960), p. 1478 (& title page).
March, "Advanced Organic Chemistry: Reactions, Mechanisms and Structure", McGraw-Hill (1968), pp. 702–709.
Maerker, Org. Reactions, 14, (1965), pp. 388, 389 and 393–395.

*Primary Examiner*—Donald G. Daus
*Assistant Examiner*—Diana G. Rivers
*Attorney, Agent, or Firm*—Bernard, Rothwell Brown

[57] ABSTRACT

Disclosed are improved Wittig reaction processes wherein the Wittig reaction is conducted in an anisole containing solvent.

10 Claims, No Drawings

WITTIG-REACTION PROCESSES

This is a continuation of application Ser. No. 692,154, filed Jan. 17, 1985, now abandoned.

This invention relates to improved Wittig reaction processes wherein the Wittig reaction is conducted in an anisole containing solvent.

The Wittig reaction is a well known reaction for preparing olefins from organic compounds containing the carbonyl group

such as aldehydes and ketones. Since the development of the Wittig reaction reported by Wittig and Schollkopf, Ber. 87, 1318 (1954) and by Wittig and Haag Ber. 88, 1654 (1955), the reaction has been employed in preparing numerous olefins having known utility.

In the Wittig reaction, an olefin is prepared by reaction of the carbonyl compound as a first reactant with an alkylidene triphenylphosphorane as a second reactant, generally in a substantially anhydrous liquid reaction mixture under Wittig reaction conditions such that the oxygen atom of the carbonyl group of the first reactant is replaced by the alkylidene group of the second reactant to prepare the olefin. The reaction conditions include conducting the reaction in a liquid medium which is a solvent for at least one reactant, typically for both reactants, and typically also is a solvent for the $(C_6H_5)_3PO$ and olefin products of the reaction. The Wittig reaction may be represented by the following general equation:

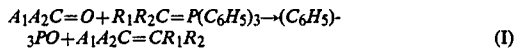

wherein each of $A_1$ and $A_2$ independently is a hydrogen atom, a halogen atom (e.g., fluorine, chlorine, bromine or iodine) or an organo group, or $A_1$ and $A_2$ conjointly with the carbonyl carbon atom constitute a cyclo-organo group and $R_2R_2C=$ is an alkylidene group in which $R_1$ is a hydrogen atom, a halogen atom (e.g., fluorine or chlorine) or an organo group and $R_2$ is a hydrogen atom or a halogen atom (e.g., fluorine or chlorine), subject to the proviso that where $R_1$ is an organo group, $R_2$ is a hydrogen atom.

Organic ethers such as ethyl ether, glymes, tetrahydrofuran and mixtures of such ethers have heretofore commonly been used as the solvent for Wittig-reaction preparation of various olefins from carbonyl compounds and alkylidene triphenylphosphorane compounds which are soluble in such ethers. However, ethyl ether is not entirely satisfactory as the solvent, especially in industrial Wittig reaction processes, since its low flash point and low boiling point result in containment thereof in the reaction mixture only with great difficulty. Glymes (e.g., glyme, diglyme, etc.) and tetrahydrofuran (THF) are not entirely satisfactory, especially on an industrial scale, since their hygroscopic properties result in obtaining and maintaining desired anhydrous conditions only with great difficulty. Moreover, it is often desirable to recover the resulting olefins from the reaction mixtures by direct extraction thereof with aqueous liquid extracting media, e.g., dilute aqueous hydrochloric acid. However, glymes and THF have such high water-solubility that olefins prepared therein are not recoverable in satisfactory amounts by direct extraction of the reaction mixtures with aqueous liquid extracting media. Increasing the amount of olefin recoverable by extraction with aqueous media from reaction mixtures containing glymes or THF solvent requires, as a practical matter, additional recovery steps of removing at least a substantial portion of the reaction mixture (e.g., by distillation of the solvent therefrom), forming a solution of the remaining olefin-containing mixture or liquor in a substantially water immiscible liquid medium and extracting the olefin from the solution by directly contacting the solution with an aqueous liquid extracting medium.

In a heretofore known application of the Wittig reaction process, the olefin narcotic antagonist 6-methylene-6-desoxy-N-cyclopropylmethyl-14-hydroxydihydronormorphine (hereinafter nalmefene) is prepared by the Wittig reaction of the carbonyl-containing compound naltrexone with methylene triphenylphosphorane in a mixture of THF and ethyl ether and direct mineral acid extraction of the resulting nalmefene. The aforesaid problems in the reaction stage and the extractive recovery stage have been found to be especially troublesome in such preparation and recovery of nalmefene.

It has now been found that olefins, e.g. nalmefene, may be prepared by Wittig reaction of anisole soluble carbonyl compounds and anisole-soluble alkylidene phosphoranes, e.g., naltrexone and methylene triphenylphosphorane, by employing anisole as the solvent in the liquid reaction mixture.

DESCRIPTION OF THE INVENTION

Generally stated, the present invention provides an improvement in Wittig reaction processes of the type set-forth above wherein the improvement comprises using anisole-soluble carbonyl compounds and anisole-soluble alkylidene triphenylphosphorane compounds as the first and second reactants, respectfully, and using anisole as at least a major portion of the Wittig reaction solvent. By this improvement, maintaining anhydrous conditions and maintaining the solvent in the liquid phase are facilitated. Another advantage of the improvement of this invention is the capability of recovering a large amount of the resulting olefin from the liquid reaction mixture by directly contacting the reaction mixture with an aqueous liquid extracting medium under extraction conditions. Accordingly, this invention effectively eliminates the need for employing additional recovery steps such as those set forth above.

DETAILED DESCRIPTION OF THE INVENTION AND OF THE MANNER AND PROCESS OF MAKING AND USING IT

The process of this invention is broadly applicable to preparing olefins by the Wittig reaction of any carbonyl compound capable of undergoing the reaction (e.g., aldehydes, ketones, and the like) as a first Wittig-reaction reactant with any alkylidene triphenylphosphorane as a second Wittig-reaction reactant such that the carbonyl oxygen atom of the first reactant is replaced by the alkylidene group of the second reactant, provided that at least one of the reactants is anisole-soluble, i.e., soluble in the amount of anisole employed. Preferably, both the reactants are anisole-soluble.

The process of this invention is accordingly applicable to the above-described Wittig reaction wherein an anisole-soluble carbonyl compound of the formula $A_1A_2C=O$ as a first reaction is reacted with an anisole-soluble alkylidene triphenylphosphorane of the formula $R_1R_2C=P(C_6H_5)_3$ as a second reactant to form an olefin of the formula $A_1A_2C=CR_1R_2$, where $A_1$, $A_2$, $R_1$ and $R_2$ are as defined above.

Included in the organo groups represented by $A_1$ and $A_2$ are cyclic and acyclic alkyl groups (e.g., methyl, ethyl, propyl, octyl, decyl, dodecyl, octadecyl, cyclopropyl, cyclobutyl and cyclohexyl); alkenyl groups (e.g., vinyl, allyl and nonadienyl); aryl groups (e.g., phenyl, naphthyl and anthracyl); aralkyl groups (eg., benzyl, xylyl and mesityl); alkaryl groups (e.g., methylphenyl and dimethyl phenyl); and substituted derivatives of the foregoing groups (e.g., carboxylated alkyl and alkenyl, hydroxylated alkyl and alkenyl, etc.). Cyclo-organo groups which can be constituted conjointly by $A_1$, $A_2$ and the carbonyl carbon atom include, illustratively, cyclopropyl, cyclobutyl, cyclohexyl, cyclohexenyl, and substituted derivatives of the foregoing. Such substituted derivatives include, illustratively, divalent-carbon containing groups which, conjointly with O=satisfying the divalency of the divalent carbon, constitute morphine derivatives such as, for example, naloxone, naltrexone, oxycodone, noroxycodone and noroxymorphone.

In embodiments of this invention where $A_1$ and $A_2$ do not conjointly with the carbonyl carbon atom constitute a cyclo-organo group, preferably at least one of $A_1$ and $A_2$ is hydrogen or methyl.

Anisole-soluble carbonyl compounds which may be effectively used as the first reactant in the process of this invention include aldehydes (for example acetaldehyde, benzaldehyde, gamma-formylcrotylacetate, fumaric ester hemialdehyde, the cyclopentane derivative of the formula:

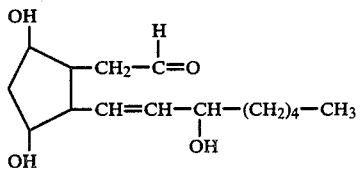
(II)

compounds of the general formula:

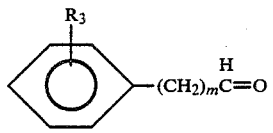
(III)

where $R_3$ is hydrogen, halo, acyl, acyloxy, nitro, amino or acylamino and m is zero or an integer of at least 1); and ketones (for example, acetone, benzophenone, cyclohexanone, methyl 4,8-diethyl-3,7-nonadiene ketone, and morphine derivatives such as, for example, naloxone, naltrexone, noroxycodone, noroxymorphone and oxycodone).

Included in the organo groups represented by $R_1$ are alkyl groups (e.g., methyl, ethyl, propyl, octyl, decyl, dodecyl and octadecyl); alkenyl groups (e.g., vinyl, allyl and vinyl-beta-ionol); aryl groups (e.g., phenyl, naphthyl and anthracyl); aralkyl groups (eg., benzyl, xylyl and mesityl); alkaryl groups (e.g., methylphenyl and dimethyl phenyl); alkoxycarbonyl (e.g., methoxy- and ethoxycarbonyl); and substituted derivatives of the foregoing groups (e.g., carboxylated and halogenated alkyl and alkenyl).

Anisole-soluble alyklidene triphenylphosphorane compounds which may be effectively used as the second reactant in the process of this invention include, for example, the methylene, ethylene, 2-propylidene, mono- and dichloromethylene, vinyl-beta-ionol, hexylidene, methoxycarbonylmethylene, and 4-methoxycarbonylbutylidene triphenylphosphoranes and fluoroalkylidene triphenylphosphoranes of the formula:

(IV)

where n is an integer of at least 1.

Examples of the utilization of the Wittig reaction in this invention include the following reactions of the indicated carbonyl compound with methylene triphenylphosphorane to prepare the indicated olefins:
(a) acetaldehyde to propylene;
(b) benzaldehyde to styrene;
(c) acetone to isobutylene;
(d) benzophenone to 1,1-diphenylethylene; and
(e) cyclohexanone to methylene cyclohexane.
The olefins have well-known utility, e.g., they can be polymerized to the corresponding polyolefins.

Additional examples include the following reactions:
(f) gamma-formylcrotylacetate with vinyl-betaionol triphenylphosphorane to prepare Vitamin A acetate;
(g) fumaric ester hemialdehyde with hexylidine triphenylphosphorane to prepare methyl 2,4-decadienoate (a pear ester fragrance);
(h) the cyclopentane derivative of Formula II above with 4-methoxycarbonylbutylidene triphenylphsophorane to prepare prostaglandin $PGF_2$, which is useful as a female hormone, e.g., for post-menopause treatment;
(i) compounds of Formula III above with compounds of Formula IV above wherein m and n are such that the sum of m+n is from 1 to 24 to prepare the corresponding terminal fluoroalkenyl benzene compounds, which are useful as pesticides, e.g., the Wittig reaction of benzaldehyde with 2-fluoroethylidene triphenylphosphorane to prepare 1-phenyl-3-fluoro-1-propene; and
(j) methyl 4,8-diethyl-3,7-nonadiene ketone with methoxycarbonylmethylene triphenylphosphorane to prepare $C_{18}$-Cecropia juvenile hormone, which is useful as an insecticide.

Yet additional examples of Wittig reactions which advantageously can be carried out in accordance with this invention include reaction of the following 6-ketomorphine derivatives with methylene triphenylphosphorane to prepare the indicated olefins:
(k) naloxone to 6-desoxy-6-methylene-N-allylnoroxymorphine, which is useful as a narcotic antagonist;
(l) naltrexone to 6-desoxy-6-methylene-N-cyclopropylmethyl-14-hydroxy-dihydro normorphine (i.e., nalmefene), which is useful as a narcotic antagonist;
(m) noroxycodone to 6-desoxy-6-methylene-noroxycodone;
(n) noroxymorphone to 6-desoxy-6-methylenenoroxymorphone; and
(o) oxycodone to 6-desoxy-6-methylene-oxycodone.
The foregoing olefin products obtained from noroxycodone, noroxymorphone and oxycodone are useful as analgesics.

In the improved Wittig reaction of the present invention, the reaction is conducted under substantially anhydrous conditions, i.e., the reaction mixture contains not more than 5% by weight water, preferably not more than 2% by weight water, and most preferably is substantially totally devoid of water.

The reaction may be conducted at any suitable temperature, e.g., from about 0° C. to about 100° C. The triphenylphosphorane reactant may be employed in any suitable amount, e.g., from about 1 to about 5 moles per mole of the carbonyl compound. The reaction is generally conducted by charging the reactants and anisole-containing solvent, which contains at least a major portion of anisole into a reaction vessel equipped with means for agitating and means for cooling the reaction mixture, and preferably with a reflux condenser for recovering solvent vapors and means for blanketing the reaction mixture with a dry inert gas, e.g., nitrogen. The reaction mixture is agitated and maintained at the desired temperature by cooling. The reaction is advantageously further controlled by slowly adding the carbonyl compound in portions to a solution of the triphenylphosphorane compound in the solvent. In general, the reaction is completed within about 0.5 to about 4 hours.

The improved process of this invention is especially advantageous for preparation of the 6-methylene morphine derivatives as set forth above in exemplary reactions k, l, m, n and o, particularly for preparing nalmefene from naltrexone. The various reaction parameters where naltrexone is the carbonyl compound and methylene triphenylphosphorane is the alkylidene triphenylphosphorane compound advantageously may be as follows: reaction temperature, about 5° to about 50° C., preferably about 20°-25° C.; about 3 to about 5 moles, preferably about 4 moles, of methylene triphenylphosphorane per mole of the 6-keto reactant (e.g., naltrexone); reaction time, about 1 to about 4 hours, typically about 2 hours; and purging of the reaction vessel with dry nitrogen.

The phosphorane compound may be prepared in situ, and in any event is preferably used in the Wittig reaction promptly after being prepared. Methods for preparing suitable phosphorane compounds are described by Maerker, *Organic Reactions,* P. 270 P. at 393-94, McGraw-Hill (1978), incorporated herein by reference.

Practice of the present invention is illustrated by the following nonlimiting examples. Throughout this disclosure, including the examples and claims which follow, all parts, percentages and other amounts given are by weight unless otherwise indicated.

Examples 1-3 are comparative examples illustrating some of the problems involved in using tetrahydrofuran and glymes in Wittig-reaction processes.

EXAMPLE 1

Tetrahydrofuran (THF) used in this example was treated by a drying procedure in which the THF was refluxed over potassium metal (using benzophenone as the indiciator) and thereafter distilled proir to use.

To a 500 ml, three-necked, roundbottom flask equipped with overhead stirring, thermometer, addition funnel and nitrogen blanket was added 150 ml of the treated THF and 20.4 grams (0.18 mol) of potassium t-butoxide. With stirring, 64.8 grams (0.18 mol) of triphenylmethylphosphonium bromide, which had been dried at 105° C. and 22 inches Hg was added. The mixture was stirred one hour to produce a bright golden ylide methylene triphenylphosphane solution.

A solution of 20.0 grams (0.06 mol) of naltrexone in 60 ml of THF was prepared and charged to the addition funnel. The above-described ylide solution was cooled to 20° C. in an ice-containing water bath and the naltrexone solution was added dropwise over a 75 minute period at such a rate to maintain the temperature in the range of 20°-25° C. The cooling bath was removed and the liquor was stirred at 20°-25° C. for two hours. The resulting slurry was again cooled in an ice-containing water bath and a solution of 10.2 grams (0.19 mol) of ammonium chloride in 50 ml of water was slowly added. An additional 50 ml of water was then added. The mixture was stirred for a few minutes and then transferred to a 500 ml separatory funnel.

The resulting layers were separated and the top (THF) layer was evaporated to a reddish-brown oil on a rotoevaporator. The bottom (aqueous) layer was extracted 2×100 ml of dichloromethane. The dichloromethane extracts and the reddish-brown oil were combined and mixed via vigorous stirring with 200 ml of water. The pH of the mixture was adjusted to 1.5 by the dropwise addition of 4 ml of concentrated hydrochloric acid solution. The layers were separated, the dichloromethane layer was again mixed with 100 ml of water and the pH was adjusted to 1.5 by the addition of a few drops of concentrated hydrochloric acid solution.

The layers were separated and the dichloromethane layer was discarded. The two aqueous layers were admixed and the resulting admixture was slowly admixed, with stirring, with 7 ml of concentrated ammonium hydroxide solution to precipitate the nalmefene. After stirring for 30 minutes, the solids were collected on a buchner funnel and washed thoroughly with water. The washed solid material was dried at 65° C. to give 17.9 grams of nalmefene (90% yield).

EXAMPLE 2

The procedure of Example 1 was repeated except that ethylene glycol dimethyl ether (glyme) was substituted for the THF as the solvent). Approximately 50% of the naltrexone remained in the reaction mixture when the reaction ceased.

EXAMPLE 3

The procedure of Example 2 was again repeated except that 2-methoxyethyl ether (diglyme) was used as the solvent. Substantially the same results were obtained as in Example 2.

EXAMPLE 4

This example illustrates improvements obtainable by the process of this invention using anisole as the solvent.

To a 500 ml, three-necked, roundbottom flask equipped with overhead drive stirring, thermometer, and means for nitrogen purge was added 150 ml of anisole and 27.2 g (0.24 mol) of potassium t-butoxide. With stirring, 86.4 g (0.24 mol) of triphenylmethylphosphonium bromide, which had been dried at 105° C. and 22" Hg, was added. The liquor was then stirred at ambient temperature for one hour.

The resulting bright yellow methylene triphenylphosp solution was cooled to 20° C. in an ice-water bath and 20.0 g (0.06 mol) of naltrexone was added in small portions at such a rate to maintain the reaction temperature at 20°-25° C. The cooling bath was removed and the golden yellow slurry was stirred for two hours at 20°-25° C. The slurry was again cooled in ice-water bath and a solution of 13.6 g (0.24 mol) of ammonium chloride in 67 ml of water was slowly added. This was followed by the addition of 67 ml of water in one portion. The mixture was stirred about fifteen minutes and transferred to a 500 ml separatory funnel. The bottom (aqueous) layer was separated and discarded.

The top (anisole) layer was mixed with 200 ml of water in a 700 ml beaker. With vigorous stirring the pH of the mixture was adjusted to 1.5 with concentrated hydrochloric acid solution. The mixture was transferred to a 1000 ml separatory funnel and the bottom (aqueous) layer was drained into a 400 ml beaker. The top (anisole) layer was discarded.

With vigorous stirring the aqueous layer was treated dropwise with concentrated ammonium hydroxide solution to pH 8.7. The mixture was stirred for about one hour to give a slurry of powdered nalmefene. The solids were collected by suction filtration and washed thoroughly with water. The washed solids were dried at 60° C. and 25" Hg to produce 17.8 g (89%) of nalmefene.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A Wittig-reaction process for preparing an olefin, which comprises the steps of:
   (a) reacting a carbonyl compound soluble in anisole as a first reactant with an alkylidene triphenylphosporane soluble in anisole as a second reactant in a substantially anhydrous liquid reaction mixture comprising an organic ether liquid medium as a solvent under Wittig-reaction conditions, said medium containing anisole as a major component,
   (b) replacing the carbonyl oxygen atom of the first reactant by the alkylidene group of the second reactant to prepare said olefin,
   (c) mixing said reaction mixture with water thereby forming an aqueous layer and an anisole containing layer,
   (d) separating said aqueous layer from the layer containing anisole, and
   (e) recovering said olefin from said aqueous layer.

2. The process of claim 1 wherein an acid is mixed with said reaction mixture and water and said olefin is precipitated from said aqueous layer by adding a base.

3. The process of claim 2 wherein said acid is hydrochloric acid or sulfuric acid.

4. The process of claim 2 wherein said base is ammonium hydroxide.

5. The process of claim 1 wherein said first reactant is naltrexone, said second reactant is methylene triphenylphosphorane and said olefin is nalmefene.

6. The process of claim 1 wherein said solvent consists essentially of anisole.

7. The process of claim 1 wherein the temperature of the reaction mixture is maintained between about 5° to about 50° C.

8. The process of claim 7 wherein the temperature of the reaction mixture is maintained between about 20° to about 25° C.

9. The process of claim 1 wherein there are between about 3 to about 5 moles of said second reactant per mole of said first reactant.

10. The process of claim 9 wherein there are about 4 moles of said second reactant per mole of said first reactant.

* * * * *

UNITED STATES PATENT AND TRADEMARK OFFICE
CERTIFICATE OF CORRECTION

PATENT NO. : 4,751,307

DATED : June 14, 1988

INVENTOR(S) : CARL R. WHITE

It is certified that error appears in the above-identified patent and that said Letters Patent is hereby corrected as shown below:

Column 1, line 43, "$R_2$" should be --$R^1$--.

Column 3, line 45 insert --and-- before "compounds".

Column 3, line 54 underline "m".

Column 4, line 14, underline "n".

Column 4, line 38, "m and n" should be underlined.

Column 4, line 39, "m + n" should be underlined.

Column 5, line 59, delete "proir" and insert --prior--.

Column 6, line 56, underline the "t".

Signed and Sealed this

Sixteenth Day of January, 1990

*Attest:*

JEFFREY M. SAMUELS

*Attesting Officer*     *Acting Commissioner of Patents and Trademarks*